(12) United States Patent
Yamamoto et al.

(10) Patent No.: US 11,883,438 B2
(45) Date of Patent: Jan. 30, 2024

(54) SPERM ACTIVATOR AND USES THEREOF

(71) Applicants: National University Corporation Nagoya University, Nagoya (JP); Gifu University, Gifu (JP); Gifu Prefecture, Gifu (JP)

(72) Inventors: Tokunori Yamamoto, Nagoya (JP); Satoshi Suzuki, Nagoya (JP); Yasuhito Funahashi, Nagoya (JP); Yoshihisa Matsukawa, Nagoya (JP); Momokazu Gotoh, Nagoya (JP); Tomohiro Kitayama, Takayama (JP); Yoichiro Hoshino, Funai-gun (JP); Tetsuma Murase, Gifu (JP)

(73) Assignees: National University Corporation Nagoya University, Nagoya (JP); Gifu University, Gifu (JP); Gifu Prefecture, Gifu (JP)

( * ) Notice: Subject to any disclaimer, the term of this patent is extended or adjusted under 35 U.S.C. 154(b) by 1378 days.

(21) Appl. No.: 16/327,817

(22) PCT Filed: Aug. 23, 2017

(86) PCT No.: PCT/JP2017/030204
§ 371 (c)(1),
(2) Date: Feb. 23, 2019

(87) PCT Pub. No.: WO2018/038180
PCT Pub. Date: Mar. 1, 2018

(65) Prior Publication Data
US 2019/0240260 A1     Aug. 8, 2019

(30) Foreign Application Priority Data
Aug. 24, 2016 (JP) ................................ 2016-164159

(51) Int. Cl.
| | | |
|---|---|---|
| *A61K 35/50* | (2015.01) | |
| *A61K 35/51* | (2015.01) | |
| *A61K 35/52* | (2015.01) | |
| *A61P 15/08* | (2006.01) | |
| *A61K 35/32* | (2015.01) | |
| *A61K 35/54* | (2015.01) | |
| *A61K 35/28* | (2015.01) | |
| *A61K 35/35* | (2015.01) | |
| *A61D 19/00* | (2006.01) | |
| *A61D 19/02* | (2006.01) | |
| *A61K 35/00* | (2006.01) | |
| *C12N 5/076* | (2010.01) | |
| *C12N 5/0775* | (2010.01) | |

(52) U.S. Cl.
CPC .............. *A61K 35/50* (2013.01); *A61D 19/00* (2013.01); *A61D 19/02* (2013.01); *A61K 35/00* (2013.01); *A61K 35/28* (2013.01); *A61K 35/32* (2013.01); *A61K 35/35* (2013.01); *A61K 35/51* (2013.01); *A61K 35/52* (2013.01); *A61K 35/54* (2013.01); *A61P 15/08* (2018.01); *C12N 5/061* (2013.01); *C12N 5/0664* (2013.01); *C12N 5/0665* (2013.01); *C12N 5/0667* (2013.01); *C12N 2500/80* (2013.01)

(58) Field of Classification Search
None
See application file for complete search history.

(56) References Cited

U.S. PATENT DOCUMENTS

2016/0108370 A1* 4/2016 Greco .................... A61K 35/12
435/375

FOREIGN PATENT DOCUMENTS

| JP | 2015-082987 A | 4/2015 |
| JP | 2016-007161 A | 1/2016 |
| JP | 2017-025038 A | 2/2017 |

OTHER PUBLICATIONS

Djouad et al., Stem Cells, 2007; 25: 2025-2032 (Year: 2007).*
Katsuda et al., Methods in Molecular Biology (2015) 1212: 171-181 (Year: 2015).*
Albersen et al., The Journal of Sexual Medicine vol. 7, Issue 10, Oct. 2010, pp. 3331-3340 (Year: 2010).*
Sato et al., Cell Proliferation, 2015 48: 671-681 (Year: 2015).*
Velarde et al., Front. Bioeng. Biotechnol. 8:117. doi: 10.3389/fbioe. 2020.00117 (Year: 2020).*
Velpula et al., Cell Cycle, 11:12, 2303-2313, DOI: 10.4161/cc. 20766 (Year: 2012).*
Mohammadi et al., International Journal of Hematology-Oncology and Stem Cell Research; Jul. 2016, 10: 161-171 (Year: 2016).*
Lyahyai et al., BMC Veterinary Research 2012, 8:169 (Year: 2012).*
Raymond Gabler and Mary Ryan, "Processing Cell Lysate with Tangential Flow Filtration": ACS Symposium Series; 1985, American Chemical Society: Washington, DC (Year: 1985).*
H. Fazaeli et al., "Introducing of a New Experimental Method in Semen Preparation: Supernatant Product of Adipose Tissue: Derived Mesenchymal Stem Cells (SPAS)", Journal of Fertilization: In Vitro—IVF-Worldwide, Reproductive Medicine, Genetics & Stem Cell Biology, vol. 04, No. 02, Apr. 3, 2016, p. 1000178 (7 pages) (cited in the Feb. 24, 2020 Search Report issued for EP17 84 3658.0).
X-G. Zhang et al., "Association of heat shock protein 90 with motility of post-thawed sperm in bulls", Cryobiology, Academic Press Inc, US, vol. 70, No. 2, Jan. 9, 2015, pp. 164-169. (cited in the Feb. 24, 2020 Search Report Issued for EP17 84 3658.0).

(Continued)

*Primary Examiner* — Christina M Borgeest
(74) *Attorney, Agent, or Firm* — Locke Lord LLP

(57) ABSTRACT

It is an object to provide a technique useful for embryo transfer and development of reproductive medical care. Provided are a sperm activator containing a disrupted product of one or more cells selected from the group consisting of adipose tissue-derived stem cells, dental pulp-derived stem cells, bone marrow-derived stem cells, and umbilical cord blood-derived stem cells as an active ingredient, and an artificial insemination method utilizing the same.

8 Claims, 5 Drawing Sheets

(56) References Cited

OTHER PUBLICATIONS

Supplementary European Search Report completed Feb. 6, 2020, issued for European patent application No. 17 84 3658.0.
B. Ling et al., "Effect of conditioned medium of mesenchymal stem cells on the in vitro maturation and subsequent development of mouse oocyte," Brazillian Journal of Medical and Biological Research, 2008, vol. 41, No. 11, pp. 978-985. (cited in the ISR).
International Search Report dated Sep. 26, 2017, issued for PCT/JP2017/030204.

* cited by examiner

SPERM ACTIVATOR AND USES THEREOF

TECHNICAL FIELD

The present invention relates to a technique that can be used in the livestock field and the medical (reproductive medical) field. More specifically, the present invention relates to a sperm activator and uses thereof. This application claims priority based on Japanese Patent Application No. 2016-164159 filed on Aug. 24, 2016, the entire contents of which are incorporated by reference.

BACKGROUND ART

In cattle production, embryo transfer technique has been developed, and embryos of Japanese black beef cattle are often transferred into the uterus of Holstein dairy cattle. According to this technique, the born calves are Japanese black cattle that will have high value as beef, while Holstein mothers that have given birth begin to lactate (that is, it is possible to start milking), so that it serves a dual purpose. In this technique, first, female beef cattle are artificially inseminated with semen of male beef cattle, and embryos are taken out from the uterus, then transferred into the uterus of dairy cattle. It is necessary to select normal embryos for transfer, but the number of transferable embryos that can be collected from beef cattle subjected to artificial insemination varies greatly from collection to collection, and a sufficient number of transferable embryos may not be obtained.

On the other hand, in Holstein dairy cattle, it is necessary to produce heifers as successors, and it is desirable that Holstein calves born be females, because male Holstein calves are not be able to milk and have low value as beef. However, the percentage of male and female calves born is approximately 50% each in ordinary artificial insemination. In response to this demand, in recent years, a method of sorting out from semen only a sperm (X sperm) in which an embryo becomes female when fertilized (an Y sperm in which an embryo becomes male and a X sperm in which an embryo becomes female are separated by a flow cytometer, and only the X sperm is cryopreserved for artificial insemination) has been developed, and frozen semen (sex-sorted semen) obtained by this method is sold. However, since sperm motility declines in the sorting process, such "sex-sorted semen" currently has a lower conception rate than ordinary frozen semen. Although a method for improving the conception rate of sex-sorted semen has been developed, the conception rate of sex-sorted semen has not yet reached the conception rate of ordinary frozen semen.

Incidentally, the present applicants have studied under the hypothesis that an adipose tissue-derived stem cell (called adipose-derived stem cell: ASC, adipose-derived regeneration cell: ADRC, adipose-derived mesenchymal stem cell: AT-MSC, AD-MSC, or the like) has a role of feeder cell and also actively acts on the reproductive process to find that ASC has the effect of activating sperm and ovum in vitro, and filed patent applications (PTLs 1, 2).

CITATION LIST

Patent Literatures

[PTL 1] JP 2015-82987 A
[PTL 2] JP 2016-7161 A

SUMMARY OF INVENTION

Technical Problem

In transfer of embryo of Japanese black beef cattle, while it is desirable to stably collect a large number of transferable embryos at a high rate, many points remain to be resolved such that the number of collections of embryos decreases, and the number of collections fluctuates greatly. On the other hand, while sex-sorted semen of Holstein dairy cattle is prepared for the purpose of giving birth to only female calves (individuals who will produce milk in the future) and is sold as frozen semen, the conception rate is lower than that of ordinary frozen semen as described above, and improvement of conception rate is strongly demanded.

Besides cattle, there is also a demand for improvement in motility rate of sperm and conception rate, for artificial insemination of other domestic animals. For example, due to rise in room temperature in summer, a decrease in motility rate of porcine sperm called summer infertility occurs every summer, causing instability in supplying semen for artificial insemination. On the other hand, many couples suffer from infertility in modern society, and thus there is a great need for the coping (treating) method. Among infertility, one whose main cause is found in male is called male infertility. As one of male infertility, there is a pathology of varicocele that an increase in testicular temperature due to scrotal venous reflux or stasis decreases a sperm motility rate.

An object of the present invention is to respond to the above demands in the livestock field and the medical field to contribute to improvement and development of embryo transfer and reproductive medicine.

Solution to Problem

As a result of extensive studies to solve the above problems, surprising findings and results that a disrupted cell suspension of ASC (in particular, filtrate which is a filtered disrupted cell suspension) activates sperms in vitro and promote fertilization and early development of an artificially inseminated ovum in vivo have been obtained. The fact that such utility value was found in the disrupted cell suspension rather than the ASC itself is extremely significant, in view of practical advantages, such that since there is no need to start cell culture at the timing of use, it is easy to prepare and handle it, and since the material (that is, ASC) can be prepared in advance, the preparation time at the time of use can be short. Incidentally, when the ASC itself, which is a living cell, is used, it has taken several days (usually at least 3 days of culture) to prepare the cells, but in the case of the disrupted cell suspension, the time required for preparation at the time of use can be shortened to about 1 hour, by preserving previously cultured cells, which makes it possible to prepare cells immediately before use.

On the other hand, the same effect as the effect of a disrupted cell suspension of ASC (that is, activation of sperm) is also recognized in disrupted suspensions of dental pulp-derived stem cells (DPSC), bone marrow-derived stem cells (BM-MSC) and umbilical cord blood-derived stem cells (CB-MSC). In addition, by further studies, it has been succeeded in identifying HSP90α as a component contained in a large amount in a disrupted cell suspension, and it was also confirmed that HSP90α actually activates sperms.

The following invention has been completed mainly based on the above results and discussion.

[1] A sperm activator whose active ingredient is a disrupted product of one or more cells selected from the group consisting of adipose tissue-derived stem cells, dental pulp-derived stem cells, bone marrow-derived stem cells, and umbilical cord blood-derived stem cells.

[2] The sperm activator according to [1], comprising any one of the following (a) to (d);
(a) cells in a frozen state,
(b) a disrupted suspension obtained by disrupting cells,
(c) a supernatant obtained by centrifuging the disrupted suspension (b), and
(d) filtrate obtained by filtering the disrupted suspension (b) or the supernatant (c).

[3] The sperm activator according to [1] or [2], which is used for artificial insemination.

[4] The sperm activator according to any one of [1] to [3], wherein a species of the cells and a species of sperm to be activated by the sperm activator are the same.

[5] The sperm activator according to any one of [1] to [4], wherein the species of the cells is a non-human mammal.

[6] The sperm activator according to [5], wherein the non-human mammal is a bovine, pig, horse, goat or sheep.

[7] The sperm activator according to any one of [1] to [4], wherein the species of the cells is human.

[8] A preparation for artificial insemination, comprising the sperm activator according to [1] or [2] filled in a container.

[9] A preparation for artificial insemination, comprising the sperm activator according to [1] or [2] and semen.

[10] A preparation for artificial insemination, comprising a mixture of the sperm activator according to [1] or [2] and semen filled in a container.

[11] A preparation for artificial insemination in which a first composition including the sperm activator according to [1] or [2] and a second composition including semen exist in a same container, wherein the first composition and the second composition exist as separate compartments in the container.

[12] An artificial insemination method, comprising injecting sperms into a uterus of a non-human mammal together with the sperm activator according to any one of [1] to [6].

[13] The artificial insemination method according to [12], wherein the sperm is sex-sorted semen.

[14] A method for producing an embryo by the artificial insemination method according to [12] or [13].

[15] An embryo produced by the artificial insemination method according to [12] or [13].

[16] An in-vitro fertilization method, comprising allowing sperms to coexist with an ovum in vitro, in the presence of the sperm activator according to any one of [1] to [7].

[17] An in-vitro fertilization method, comprising allowing sperms treated with the sperm activator according to any one of [1] to [7] to coexist with an ovum in vitro.

[18] A sperm activation method, comprising the following step (1):
(1) culturing sperms in the presence of the sperm activator according to any one of [1] to [7].

[19] The sperm activation method according to [18], further comprising the following step (2):
(2) recovering the cultured sperms.

DESCRIPTION OF EMBODIMENTS

1. Sperm Activator

Figure 1:
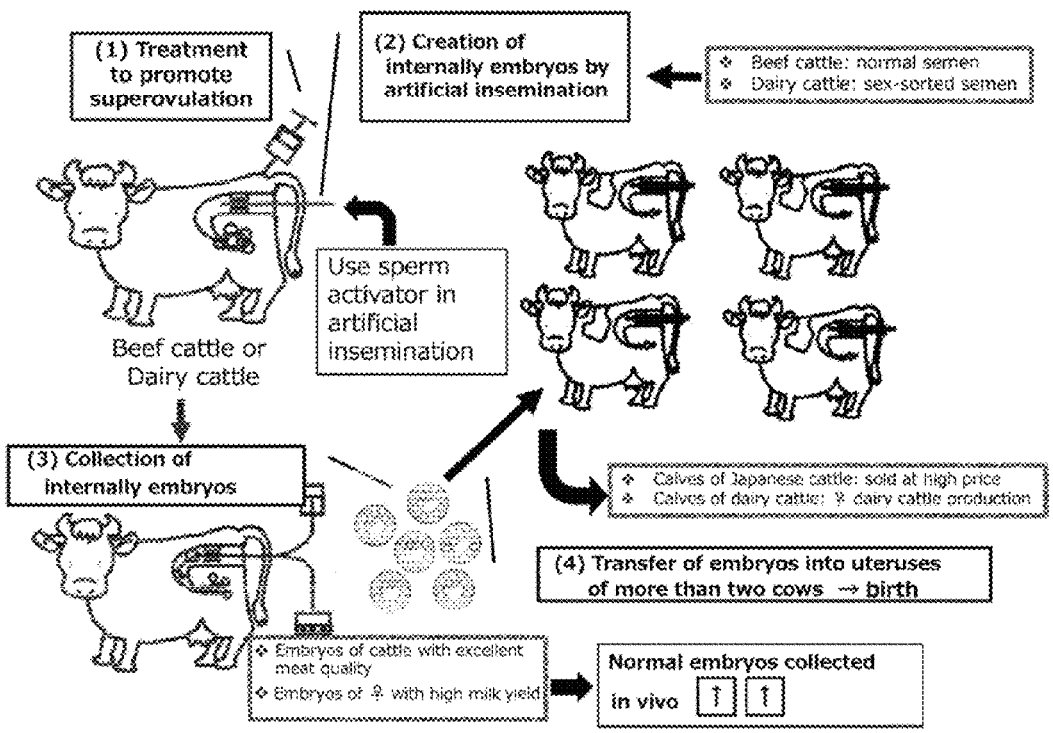
FIG. 1 An outline of embryo transfer in cattle.

A first aspect of the present invention relates to a sperm activator. The term "activation" as used for a sperm means that sperm motility/motility rate (especially, progressive motility/progressive motility rate) increases and/or sperm lifespan increases. Suppressing the decrease in motility/motility rate and maintaining high motility/motility rate also fall under "motility/motility rate increases" herein. By using activated sperms, for example, improvement of fertilization efficiency and conception rate in artificial insemination, promotion of early development, and the like can be expected.

In the sperm activator of the present invention, a disrupted product of adipose tissue-derived stem cells (ASCs) is used as an active ingredient. In other words, components in the disrupted product of ASC bring about a characteristic effect, namely, activation of a sperm. In this respect, it is the opposite of the technique that utilizes ASC itself (that is, living cell) for activation of sperm.

In one embodiment of the sperm activator of the present invention, a disrupted product of dental pulp-derived stem cells (DPSC), human bone marrow-derived stem cells (BM-MSC), or umbilical cord blood-derived stem cells (CB-MSC) is used as an active ingredient.

Two or more types among the disrupted product of adipose tissue-derived stem cells (ASC), the disrupted product of dental pulp-derived stem cells (DPSC), the disrupted product of human bone marrow-derived stem cells (BM-MSC) and the disrupted product of umbilical cord blood-derived stem cells (CB-MSC) may be used in combination to constitute the sperm activator of the present invention.

When using the disrupted product of adipose tissue-derived stem cells (ASC) as the active ingredient, the sperm activator of the present invention will typically contain any of the following (a) to (d).
(a) adipose tissue-derived stem cells (ASC) in a frozen state
(b) a disrupted suspension obtained by disrupting adipose tissue-derived stem cells (ASC)
(c) a supernatant obtained by centrifuging the disrupted suspension (b)
(d) filtrate obtained by filtering the disrupted suspension (b) or the supernatant (c)

In the case of containing (a), that is, "adipose tissue-derived stem cells (ASC) in a frozen state", ASC will be disrupted by thawing before use or during use to produce "disrupted product of ASC" that acts as an active ingredient. The sperm activator of this embodiment has many advantages such as no need for preparation at the time of use, easy handling, and suitability for long-term preservation. In order to prepare the sperm activator of this embodiment, ASC may be placed in a suitable container (for example, tube suitable for cryopreservation, centrifuge tube, bag, etc.) and frozen (for example, −20° C. to −196° C.). A method for preparing ASC will be described later.

In order to obtain (b), that is, "a disrupted suspension obtained by disrupting adipose tissue-derived stem cells (ASC)", ASC may be subjected to disruption treatment, for example, freeze-thaw treatment (treatment of thawing after freezing), ultrasonic treatment, treatment with a French press or a homogenizer, or the like. The cells may be disrupted by non-physical treatment. In addition, as the cells to be subjected to disruption treatment, not only living cells but also dead cells or damaged cells may be used. Among various kinds of disruption treatments, freeze-thaw treatment is particularly preferable in that it is simple, and it is hygienic because contamination due to contact between an instrument and the cells can be avoided. The freeze-thaw treatment may be repeated a plurality of times (for example, 2 to 5 times). The conditions for freezing in the freeze-thaw treatment are not particularly limited, but it may be frozen, for example, at −20° C. to −196° C. The conditions for thawing are also not particularly limited. For example, thawing in hot water (for example, 35° C. to 40° C.), thawing at room temperature, or the like can be adopted.

In one embodiment of the present invention, a supernatant ((c)) obtained by centrifuging the disrupted suspension ((b)), that is, one obtained by removing insoluble components from the disrupted suspension is used for the sperm activator. Removal of insoluble components may not be complete removal. The conditions of the centrifugal treatment are exemplified as 200 to 300 g for 5 minutes to 10 minutes.

In another embodiment of the present invention, the filtrate obtained by filtering the disrupted suspension ((b)) or its centrifuged supernatant ((c)) is used for the sperm activator. Unnecessary components can be removed by filtering. Also, by using a filter with an appropriate pore size, removal of unnecessary components and sterilization treatment can be performed at the same time. Material, pore size, and the like of the filter used for filtering are not particularly limited. However, cellulose acetate can be exemplified as a preferable material. A filter made of metal may be used. An example of the pore size is 0.2 µm to 0.45 µm.

Also in the case of using the disrupted product of dental pulp-derived stem cells (DPSC), human bone marrow-derived stem cells (BM-MSC), or umbilical cord blood-derived stem cells (CB-MSC) as the active ingredient, the sperm activator will typically contain any of (a) cells in a frozen state, (b) a disrupted suspension obtained by disrupting cells, (c) a supernatant obtained by centrifuging the disrupted suspension, and (d) filtrate obtained by filtering the disrupted suspension or the supernatant, similarly to the case of using the disrupted product of adipose tissue-derived stem cells (ASC) as the active ingredient. The preparation methods and the like of (a) to (d) of this embodiment are the same as the case where the disrupted product of adipose tissue-derived stem cells (ASC) is used as the active ingredient, and thus the explanation is omitted.

The sperm activator may contain a protective agent such as dimethyl sulfoxide (DMSO) or serum albumin, an antibiotic, vitamins, a carrier, an excipient, a disintegrant, a buffer, an emulsifier, a suspension, a soothing agent, a stabilizer, a preservative, an antiseptic, a physiological saline solution, or the like.

The origin of the cells (that is, ASC, DPSC, BM-MSC, CB-MSC) used in the sperm activator of the present invention, that is, the species, is not particularly limited, and is preferably specified and determined considering the use of the sperm activator. For example, when used for activation of bovine sperms, it is preferable to use bovine cells. Likewise, when used for activation of human sperms, it is preferable to use human cells. Thus, preferably, the species of the cells used for the sperm activator is the same as the species of the sperm. However, as far as the desired effect, that is, activation of sperms is achieved, the origins of the cells and sperms may be different. Examples of the origin (species) of cells include a bovine, pig, horse, goat, sheep, human, monkey, dog, cat, mouse, rat, guinea pig, and hamster. Also, examples of the origin (species) of sperms include a bovine, pig, horse, goat, sheep, human, monkey, dog, cat, mouse, rat, guinea pig, hamster, birds (chicken, quail, duck, etc.), and fish (salmon, trout, tuna, bonito, etc.). In one embodiment, sperms of a domestic animal (for example, bovine, pig, horse, goat, sheep) that is a non-human mammal are used. In another embodiment, human sperms are used.

ASC may be prepared according to a conventional method. ASC is widely used for various uses, and those skilled in the art can easily prepare ASC with reference to literature and books. Cells issued from a public cell bank, commercially available cells, or the like may be used. DPSC, BM-MSC, and CB-MSC may also be similarly prepared according to a conventional method. These cells are also widely used for various uses, and those skilled in the art can easily prepare them with reference to literature and books, and cells issued from a public cell bank, commercially available cells, or the like may be used. Hereinafter, as an example of a preparation method of cells, a preparation method of ASC (one example) and a preparation method of DPSC (one example) will be described.

<Preparation Method of ASC>

"The adipose tissue-derived stem cells (ASC)" in the present invention refers to somatic stem cells that are contained in an adipose tissue, and cells that are obtained by culture of the somatic stem cells (including subculture) also correspond to "the adipose tissue-derived stem cells (ASC)" as long as such cells maintain multipotency. Generally, ASC is obtained from an adipose tissue separated from a living body as a starting material, and prepared into "an isolated state" as a cell that constitutes a cell population (containing cells except for ASC, which are originated from the adipose tissue). "An isolated state" herein means that ASC is present in a state of being taken out from its original environment (that is, a state of constituting a part of a living body), in other words, a state of being different from an original state of its existence due to artificial manipulation. Note that adipose tissue-derived mesenchymal stem cells are also called ADRC (adipose-derived regeneration cells), AT-MSC (adipose-derived mesenchymal stem cells), AD-MSC (adipose-derived mesenchymal stem cells), and so on. In the present specification, the following terms, that is, adipose tissue-derived mesenchymal stem cells, ASC, ADRC, AT-MSC, and AD-MSC are used exchangeably.

ASC is prepared through steps such as separation of stem cells from a fat substrate, washing, concentration, and culture. A preparation method of ASC is not particularly limited. For example, ASC can be prepared according to, for example, known methods (Fraser J K et al. (2006), Fat tissue: an underappreciated source of stem cells for biotechnology. Trends in Biotechnology; April; 24(4): 150-4. Epub 2006 Feb. 20. Review; Zuk P A et al. (2002), Human adipose tissue is a source of multipotent stem cells. Molecular Biology of the Cell; December; 13(12): 4279-95; Zuk P A et al. (2001), Multilineage cells from human adipose tissue: implications for cell-based therapies. Tissue Engineering; April; 7(2): 211-28, and the like are served as references). Further, a device for preparing ASC from adipose tissues (for example, Celution (registered trademark) device (Cytori Therapeutics, Inc., USA, San Diego)) is also commercially available and ASC may be prepared using the device. When the device is used, cells that are cell surface marker CD29 and CD44 positive can be separated from adipose tissues. Specific examples of a preparation method of ASC are shown below.

(1) Preparation of Population of Cells from Adipose Tissue

Adipose tissue can be obtained from an animal by means such as excision and suck. The term "animal" herein includes human and non-human mammalians (pet animals, domestic animal, and experimental animal. Specifically examples include monkey, pig, cattle/cow, horse, goat, sheep, dog, cat, mouse, rat, guinea pig, hamster, and the like). In a case where the activated sperm obtained by the method of the present invention is used for the purpose of treatment, in order to avoid the problem of immunological rejection, it is preferable that adipose tissue is collected from the same individuals as subjects (recipients) to which the activated sperm is to be administered. However, adipose tissue of the same kinds of animals (other animals) or adipose tissue heterogeneous animals may be used.

An example of adipose tissue can include subcutaneous fat, offal fat, intramuscular fat, and inter-muscular fat. Among them, subcutaneous fat is a preferable cell source because it can be collected under local anesthesia in an extremely simple and easy manner and therefore the burden to a doner in collection is small. In general, one kind of adipose tissue is used, but two kinds or more of adipose tissues can be used. Furthermore, adipose tissues (which may not be the same kind of adipose tissue) collected in a plurality of times may be mixed and used in the later operation. The collection amount of adipose tissue can be determined by considering the kind of donors or kinds of tissue, or the necessary amount of ASCs. For example, the amount can be from 0.5 g-500 g. When a donor is human, it is preferable that the collection amount at one time is about 10 g-20 g or less by considering a burden to the donor. The collected adipose tissue is subjected to removal of blood components attached thereto and stripping if necessary and thereafter, subjected to the following enzyme treatment. Note here that by washing adipose tissue with appropriate buffer solution or culture solution, blood components can be removed.

The enzyme treatment is carried out by digesting adipose tissue with protease such as collagenase, trypsin and Dispase. Such an enzyme treatment may be carried out by techniques and conditions that are known to a person skilled in the art (see, for example, R. I. Freshney, Culture of Animal Cells: A Manual of Basic Technique, 4th Edition, A John Wiley & Sones Inc., Publication). A cell population obtained by the above-mentioned enzyme treatment includes multipotent stem cells, endothelial cells, interstitial cells, blood corpuscle cells, and/or precursor cells thereof. The kinds or ratios of the cells constituting the cell population depend upon the origin and kinds of adipose tissue to be used.

(2) Obtaining of Sedimented Cell Population (SVF Fraction: Stromal Vascular Fractions)

The cell population is then subjected to centrifugation. Sediments obtained by centrifugation are collected as sedimented cell population (also referred to as "SVF fraction" in this specification). The conditions of centrifugation are different depending upon the kinds or amount of cells. The centrifugation is carried out for example, at 800-1500 rpm for 1-10 minutes. Prior to the centrifugation, cell population after enzyme treatment can be subjected to filtration and tissue that has not been digested with enzyme contained therein can be removed.

The "SVF fraction" obtained herein includes ASCs. Therefore, the SVF fraction can be used for a co-culture with sperm. The kinds or ratio of cells constituting the SVF fraction depend upon the origin and kinds of adipose tissue to be used, conditions of the enzyme treatment, and the like. The characteristics of the SVF fraction are showed in the International Publication WO2006/006692A1.

(3) Selective Culture of Adhesive Cells (ASC) and Recovery of Cells

Other cell components (such as endothelial cells, stroma cells, hematopoietic cells, and precursor cells thereof) are contained in a SVF fraction other than ASC. Thus, in one embodiment of the present invention, unnecessary cell components are removed from the SVF fraction by carrying out the following selective culture. Then, cells that are obtained as a result are used in the present invention as ASC.

Firstly, a SVF fraction is suspended in an appropriate medium, and then seeded on a culture dish and cultured overnight. Floating cells (non-adhesive cells) are removed by replacement of a medium. Then, culture is continued while suitable replacement of a medium (for example, once per 2-3 days). Subculture is carried out according to necessity. The passage number is not particularly limited. However, it is not preferable to excessively run over the subculture from the view point of maintenance of pluripotency and proliferation potency (preferably up to the fifth passage). Note that, for the culture medium, a medium for normal animal cell culture can be used. Examples such as Dulbecco's modified Eagle's Medium (DMEM) (NISSUI PHARMACEUTICAL, etc.), α-MEM (Dainippon Seiyaku, etc.), DMED: Ham's F12 mixed medium (1:1) (Dainippon Seiyaku, etc.), Ham's F12 medium (Dainippon Seiyaku, etc.), and MCDB 201 medium (Research Institute for the Functional Peptides) can be used. Media added with serums (fetal bovine serum, human serum, sheep serum, etc.) or serum replacement s (Knockout serum replacement (KSR), etc.) may also be used. The adding amount of a serum or serum replacement can be set within the range from 5% (v/v)-30% (v/v), for example.

Adhesive cells selectively survive and proliferate according to the above mentioned operations. Next, the cells proliferated are collected. The cells may be collected by routine procedures and, for example, collected easily by enzyme treatment (treatment with trypsin or Dispase) and then cells are scraped out by using a cell scraper, a pipette, or the like. Furthermore, when sheet culture is carried out by using a commercially available temperature sensitive culture dish, cells may be collected in a sheet shape without carrying out enzyme treatment. Use of thus collected cells (ASC) makes it possible to prepare a cell population containing ASC at high purity.

(4) Low-Serum Culture (Selective Culture in a Low-Serum Medium) and Collection of Cells In one embodiment of the present invention, the following low-serum culture is carried out in place of or after (3) mentioned above. Then, the cells obtained as a result are used as ASC n the present invention.

In low-serum culture, the SVF fraction (when this step is carried out after (3), the cells that are collected in (3) are used) is cultured under the low-serum conditions and a desired multipotent stem cell (that is, ASC) is selectively proliferated. Since the amount of serum to be used is small in the low-serum culture method, in a case where the activated sperm obtained by the method of the present invention is used for the purpose of treatment, it is possible to use the serum of the subjects (recipients) themselves. That is to say, culture using autoserum can be carried. The "under low-serum conditions" herein denotes conditions in which a medium contains not more than 5% serum. Preferably, the sedimented cell population is cultured in a culture solution containing not more than 2% (V/V) serum. More preferably, the cells are cultured in a culture solution containing not more than 2% (V/V) serum and 1-100 ng/ml of fibroblast growth factor-2 (bFGF).

The serum is not limited to fetal bovine serum. Human serum, sheep serum, and the like, can be used. In a case where the activated sperm obtained by the method of the present invention is used for treatment of human, preferably, the human serum, more preferably the serum of a subject of the treatment (that is to say, autoserum) is used.

As the medium, a medium for culturing animal cells can be used on condition that the amount of serum contained in the use is low. For example, Dulbecco's modified Eagle's Medium (DMEM) (NISSUI PHARMACEUTICAL, etc.), α-MEM (Dainippon Seiyaku, etc.), DMED: Ham's:F12 mixed medium (1:1) (Dainippon Seiyaku etc.), Ham's F12 medium (Dainippon Seiyaku, etc.), MCDB201 medium (Research Institute for the Functional Peptides), and the like, can be used.

By culturing by the above-mentioned method, multipotent stem cells (ASCs) can be selectively proliferated. Furthermore, since the multipotent stem cells (ASCs) proliferated in the above-mentioned culture conditions have a high proliferation activity, it is possible to easily prepare cells necessary in number for the present invention by subculture. Note here that the characteristics of the cells selectively proliferated by low-serum culture of SVF fraction are shown in the International Publication WO2006/006692A1.

Subsequently, selectively proliferated cells by the above-mentioned low-serum culture are collected. A collection operation may be carried out in the same manner as in the case of (3). Use of thus collected cells (ASC) makes it possible to prepare a cell population containing ASC at high purity.

In the above-mentioned method, the cells proliferated by low-serum culture of SVF fraction is used for the present invention. However, cells proliferated by the low serum culture of cell population obtained from adipose tissue (without carrying out centrifugation for obtaining SVF fraction) can be used as ASCs. That is to say, in one embodiment of the present invention, cells proliferated by the low-serum culture of cell population obtained from adipose tissue are used as low-serum culture ASCs. Not multipotent stem cells that are obtained according to selective culture ((3) and (4) mentioned above) but a SVF fraction (containing adipose tissue-derived mesenchymal stem cells) can be directly used. Note that "directly used" herein means that a SVF fraction is used in the present invention without undergoing selective culture.

<Preparation Method of DPSC>

Dental pulp-derived stem cells (DPSCs) and stem cells from exfoliated deciduous teeth (SHED) have been identified as novel stem cell population having both self-proliferation ability and pluripotency (S. Gronthos, M. Mankani, J. Brahim, P. G. Robey, S. Shi, Postnatal human dental pulp stem cells (DPSCs) in vitro and in vivo, Proc. Natl. Acad. Sci. U.S.A 97 (2000) 13625-30; M. Miura, S. Gronthos, M. Zhao, B. Lu, L. W. Fisher, P. G. Robey, S. Shi, SHED: Stem cells from human exfoliated deciduous teeth, Proc. Natl. Acad. Sci. U.S.A 100 (2003) 5807-12; WO 2006/010600 A).

An example of a method of collecting and preparing dental pulp stem cells is shown below. In this collection and preparation method, (1) collection of dental pulp, (2) enzyme treatment, (3) cell culture, and (4) collection of cells are performed in order.

(1) Collection of Dental Pulp

A naturally-exfoliated deciduous tooth (or extracted deciduous tooth or permanent tooth) is disinfected with chlorhexidine or Isodine solution, then a crown part is split off, and a dental pulp tissue is collected with a dental reamer.

(2) Enzyme Treatment

The collected dental pulp tissue is suspended in a basal medium (10% bovine serum/antibiotic-containing Dulbecco's modified Eagle Medium), and treated with 2 mg/ml collagenase and Dispase at 37° C. for 1 hour. Dental pulp cells after enzymatic treatment are collected by centrifugation (5,000 rpm) for 5 minutes. In principle, cell sorting using a cell strainer is not used because it reduces the collection efficiency of neural stem cell fraction of SHED or DPSC.

(3) Cell Culture

The cells are re-suspended in 4 cc of the basal medium, and seeded in a culture dish for adherent cells with a diameter of 6 cm. After culturing in an incubator adjusted to 5% $CO_2$, 37° C. for 3 days, adherent cells forming colonies are treated with 0.05% trypsin.EDTA at 37° C. for 5 minutes. Dental pulp cells detached from the dish are seeded in a culture dish for adherent cells with a diameter of 10 cm and extended culture is performed. For example, when subconfluence (about 70% of the surface of the culture vessel is occupied by cells) or confluence is reached as observed with the naked eye, the cells are detached from the culture vessel and collected, and again seeded in a culture vessel filled with culture medium. Subculture may also be repeated. For example, the cells are subcultured 1 to 8 times to proliferate until the required number of cells (for example, about $1 \times 10^7$ cells/ml) is obtained. Here, the cells can be detached from the culture vessel by a conventional method such as trypsin treatment. After the culture, the cells may also be collected and stored (storage condition is, for example, −198° C.).

(4) Collection of Cells

Next, the cells are collected. The cells (DPSC) can be collected by detaching the cells from the culture vessel by trypsin treatment or the like and then subjecting the cells to centrifugation.

The sperm activator of the present invention can be provided in a form containing it alone (for example, filled in a suitable container), for example, as a preparation for artificial insemination, and also in various forms, for example, a form packed in the same container in a state of including a sperm activator and semen in separate compartments (a first compartment in which a first composition containing the sperm activator exists and a second compartment in which a second composition containing the semen exists are provided) (for example, it can take the form of a semen straw for artificial insemination), a form filled in a container in a state of mixing a sperm activator and semen (for example, it can take the form of a semen straw for artificial insemination), and the like. The container is not particularly limited, but, for example, a straw tube frequently used for artificial insemination, a centrifuge tube, or the like can be used.

2. Use of Sperm Activator

A second aspect of the present invention relates to a use of a sperm activator. The sperm activator of the present invention can be used in artificial insemination (improvement in success rate and efficiency of in-vivo fertilization and in-vitro fertilization), treatment and improvement of various diseases associated with sperm disorders or due mainly to or due secondarily to sperm disorders (for example, varicocele, male infertility, cryptorchidism, X-ray irradiation, sperm disorders after malignant tumor surgery or chemotherapy), domestic animal breeding (improvement in success rate and efficiency of artificial insemination), breeding and maintenance of species (for example, maintenance of endangered species, maintenance or crossing of pet lines), and the like. Hereinafter, particularly important uses of the sperm activator of the present invention will be described in detail. Incidentally, the uses may follow conventional methods other than the conditions characteristic of the present invention, that is, using the sperm activator of the present invention (for example, artificial insemination manual for cattle (incorporated association, livestock technology association), horse artificial insemination manual (general incorporated association, AIAJ), breeding technical manual for cattle (general incorporated association, AIAJ), domestic animal artificial insemination handbook (general incorporated association, AIAJ), and the like can be used as references).

2-1. Internal Fertilization

When applying the sperm activator of the present invention to internal fertilization, sperms will be injected into a uterus of a non-human mammal together with the sperm activator. Specifically, for example, (i) the sperm activator and sperms are mixed, and then injected into the uterus of a non-human mammal, (ii) the sperm activator and sperms are simultaneously injected into the uterus of a non-human mammal, or (ii) the sperm activator and sperms are injected separately (in random order) into the uterus of a non-human mammal.

Examples of species that is the origin of a sperm and an ovum are bovine, pig, horse, goat, sheep, birds (chicken, quail, duck, etc.), and fish (salmon, trout, tuna, bonito, etc.). In principle, the species of the sperm and the ovum are the same. However, when it is a fertile combination, the species of sperm and the species of ovum may be different.

As the sperm, sex-sorted semen may be used. In this specification, in order to distinguish it from sex-sorted semen, semen that has not been subjected to sex sorting is sometimes called "ordinary semen". The use of sex-sorted semen is useful in applying the present invention to, for example, the production of dairy cattle as described later.

The internal fertilization method of the present invention can be applied to, for example, a useful domestic animal production method. As an example, with reference to FIG. 1, the application to bovine (beef cattle, dairy cattle) production method utilizing embryo transfer will be explained. Typically, bovine embryo transfer is performed in the following procedure.

(1) Beef cattle (for example, Japanese cattle) or dairy cattle (for example, Holstein dairy cattle) are subjected to treatment (injection) to promote superovulation.

(2) In the case of beef cattle, ordinary frozen semen is artificially inseminated (that is, semen is injected into the uterus). In the case of dairy cattle, sex-sorted semen (X sperm selected for conception of a female fetus) is artificially inseminated.

(3) After about a week, embryos that reach the uterus are taken out.

(4) The collected embryos are transferred to the uterus of another cow (usually several individuals) to produce calves of beef cattle with excellent meat quality or calves (female) of dairy cattle.

The sperm activator of the present invention is used in the treatment of (2). As a result, the number of normal embryos collected in (3) increases, and the production number of calves of good beef cattle or female dairy cattle with high milk production capacity increases. The above method is merely an example of a typical production method. For example, the application of the present invention to a production method without embryo transfer, that is, a method of impregnating cows and giving birth right after internal fertilization or the like is also envisioned.

2-2. In-Vitro Fertilization

In the case of utilizing the sperm activator of the present invention for in-vitro fertilization, a state in which sperms activated by the sperm activator and an ovum coexist may be formed, or a state in which sperms and an ovum coexist in the presence of the sperm activator may be formed. The "activated sperm" used for the former can be prepared by the following method. Incidentally, in order to form a state in which sperms (activated or pre-activated sperm) and an ovum coexist, they may be placed in the same container and cultured.

Examples of species that is the origin of the sperm and the ovum are human, bovine, pig, horse, goat, sheep, birds (chicken, quail, duck, etc.), and fish (salmon, trout, tuna, bonito, etc.). In principle, the species of the sperm and the ovum are the same. However, when it is a fertile combination, the species of sperm and the species of ovum may be different. The ovum used for in-vitro fertilization may be prepared by isolation from the living body, distribution from a cell bank, or the like.

First, sperms are cultured in the presence of a sperm activator (step (1)). This step is carried out in vitro as it is clear from its definition. Culture conditions suitable for culturing sperms are preferably adopted. For example, sperms are added to medium semen (BO solution) supplemented with the sperm activator, and cultured at a temperature condition of 35° C. to 40° C. for 30 minutes to 24 hours. Sperms are activated by this culture. That is, activated sperm are obtained. In one embodiment, cultured sperms (that is, activated sperms) are recovered (step (2)), and the recovered sperms are used for in-vitro fertilization. Concentration, sorting or the like may be performed before use. Since activated sperms can be obtained according to the above method, it is said that the present application provides a sperm activation method or a method of producing or obtaining activated sperms.

As described above, in one embodiment of in-vitro fertilization utilizing the sperm activator of the present invention, a state in which sperms and an ovum coexist in the presence of the sperm activator is formed. In this case, any of (i) a method of mixing a sperm activator and an ovum, and adding sperms thereto in vitro, (ii) a method of mixing a sperm activator and sperms, and adding an ovum thereto in vitro, or (iii) a method of mixing a sperm activator, sperms and an ovum in vitro may be adopted.

EXAMPLES

A. Test in Japanese Black Cattle

<Test 1> Co-Culture of Frozen-Thawed Bovine ASC Cells (Disrupted ASC Cell Suspension) or its Centrifuged Supernatant with Bovine Sperm

1. Materials and Methods

1-1. Collection of Adipose Tissue-Derived Stem Cells (ASC)

ASC was collected from bovine frozen subcutaneous fat in accordance with the method of JP 2010-094076 A. Specifically, it was performed as follows.

(1) Collection of Adipose Tissue and Cryopreservation

At a slaughter house, subcutaneous adipose tissue (about 3 cm square) of a carcass was excised with scissors and placed in a plastic zip bag. This was charged into a dry shipper where liquid nitrogen was adsorbed to an internal adsorbent and excess liquid nitrogen was discarded, and frozen in vapor of liquid nitrogen.

(2) Thawing and Tissue Decomposition

The frozen adipose tissue contained in the plastic bag was thawed with hot water at 39° C. The thawed adipose tissue was chopped with scissors or the like and placed in a 15 ml centrifuge tube. Subsequently, Dulbecco's modified Eagle Medium (Sigma) containing 0.1 w/v % collagenase and 0.2 w/v % Dispase was added to the chopped adipose tissue in a volume of 3 to 5 times its volume. This tissue suspension was cultured with shaking on a water bath at 39° C. for 1 to 2 hours to obtain adipose tissue lysate.

(3) Cell Collection and Cell Culture

The adipose tissue lysate was centrifuged, and non-melted remaining fat and supernatant of the upper layer were discarded. The remaining precipitate was suspended in 500 μl of a primary culture medium (MF-start, registered trademark, TOYOBO CO., LTD.) supplemented with antibiotic Primocin (registered trademark, INVIVOGEN) so as to obtain a final concentration of 100 μg/ml, and the suspension was placed in a well of a 24-well plate, and cultured in a $CO_2$ incubator (5% $CO_2$, 95% air, 39° C., saturated humidity). The cells proliferated until the well became confluent, and then were detached with trypsin EDTA, and a portion of one well was divided into five wells and subcultured.

1-2. Freezing and Thawing of Bovine Semen

Bovine semen was diluted with an egg yolk-sodium citrate buffer so that the sperm concentration is about 100 million/ml, and dispensed and sealed in about 500 μl aliquots into a straw container, then frozen in liquid nitrogen vapor and stored in liquid nitrogen. This bovine frozen semen was thawed with hot water at 38° C. and used for the following test.

1-3. Production of ASC Disrupted Suspension

Bovine ASC (confluent) of a portion of one well (ASC×1) or two wells (ASC×2) of the 24-well plate was detached with trypsin EDTA, washed with PBS, and then resuspended in 500 μl of PBS. Subsequently, it was filled and sealed in a 0.5 ml capacity straw for semen cryopreservation and cryopreserved at −20° C. Each of the filled and sealed straws was thawed at 38° C. and then used as follows.

ASC×1: One thawed straw is used as it is

ASC×2: Two thawed straws are used as they are

ASC×1 centrifuged supernatant: One thawed straw is centrifuged and the obtained supernatant is used ASC×2 centrifuged supernatant: Two thawed straws are centrifuged and the obtained supernatant is used

1-4. Co-Culture of ASC Disrupted Suspension and Bovine Sperm

100 μl of bovine frozen-thawed semen and 100 μl of an ASC disrupted suspension (ASC×1, ASC×2) or ASC centrifuged supernatant (ASC×1 centrifuged supernatant, ASC×2 centrifuged supernatant) were placed in a 24-well plate, and co-cultured in a $CO_2$ incubator (5% $CO_2$, 95% air, 39° C., saturated humidity). In the control group, an egg yolk-sodium citrate buffer (containing 6.5% glycerin), primary diluent (an egg yolk-sodium citrate buffer without glycerin) or PBS was used instead of ASC disrupted suspension/ASC centrifuged supernatant.

1-5. Evaluation of Sperm Motility

The sperms were observed under a microscope at 0 hours, 3 hours, 6 hours, 8 hours, and 9 hours after the start of co-culture. Specifically, 6 μl of the co-cultured semen was dropped onto a glass slide, an 18 mm×18 mm coverslip was placed thereon, and the semen was observed under a microscope equipped with an eyepiece with a grid micrometer. Sperm motility was classified into progressive motion (PR), non-progressive motion (NP), and immobility (IM), the sperm count of each motility in 10 grids was counted, and the ratio was obtained.

2. Results

The results are shown below. An effect of increasing sperm motility is observed in the ASC disrupted suspension (ASC×1, ASC×2) and the ASC centrifuged supernatant (ASC×1 centrifuged supernatant, ASC×2 centrifuged supernatant).

TABLE 1

| Added solution | Motility (%) | | | | | | | | | | | | | | |
|---|---|---|---|---|---|---|---|---|---|---|---|---|---|---|---|
| | 0 h | | | 3 h | | | 6 h | | | 8 h | | | 9 h | | |
| | PR | NP | IM | PR | NP | IM | PR | NP | IM | PR | NP | IM | PR | NP | IM |
| egg yolk sodium citrate buffer (containing glycerin) | 28 | 35 | 38 | 17 | 4 | 79 | 0 | 16 | 84 | 0 | 0 | 100 | | | |
| Primary diluent (without glycerin) | | | | 15 | 5 | 80 | 0 | 18 | 82 | 0 | 0 | 100 | | | |
| PBS | | | | 15 | 5 | 80 | 0 | 13 | 87 | 0 | 0 | 100 | | | |
| ASC × 1 | | | | 22 | 4 | 74 | 13 | 4 | 83 | 0 | 20 | 80 | 0 | 19 | 81 |
| ASC × 2 | | | | 22 | 0 | 78 | 22 | 4 | 74 | 21 | 4 | 75 | 9 | 5 | 86 |

TABLE 1-continued

| Added solution | Motility (%) | | | | | | | | | | | | | | |
|---|---|---|---|---|---|---|---|---|---|---|---|---|---|---|---|
| | 0 h | | | 3 h | | | 6 h | | | 8 h | | | 9 h | | |
| | PR | NP | IM | PR | NP | IM | PR | NP | IM | PR | NP | IM | PR | NP | IM |
| ASC × 1 centrifuged supernatant | | | | 27 | 0 | 73 | 14 | 5 | 81 | 0 | 24 | 76 | 0 | 19 | 81 |
| ASC × 2 centrifuged supernatant | | | | 41 | 6 | 53 | 15 | 4 | 81 | 17 | 0 | 83 | 8 | 4 | 88 |

<Test 2> Effect of Japanese Black Cattle ASC Filtrate
1. Materials and Methods
1-1. Collection and Culture of ASC An adipose tissue was collected from a bovine dorsal subcutaneous tissue at a slaughter house (1 to 3 g). The adipose tissue was taken back to a laboratory, and chopped with scissors or the like and placed in a 50 ml centrifuge tube. Dulbecco's modified Eagle Medium (Sigma) containing 0.1% by weight collagenase and 0.2 w/v % Dispase was added to the chopped adipose tissue in a volume of 3 to 5 times its volume. This tissue suspension was cultured with shaking on a water bath at 39° C. for 1 to 2 hours to obtain adipose tissue lysate. The adipose tissue lysate was centrifuged, and non-melted remaining fat and supernatant of the upper layer were discarded. The remaining precipitate was suspended in MesenPro culture medium supplemented with 20% FCS, placed in a 10 cm plate, and cultured in a $CO_2$ incubator (5% $CO_2$, 95% air, 39° C., saturated humidity). After confluence, the cells were detached with trypsin/EDTA and subcultured to one to five 10 cm plates.

1-2. Production of ASC Solution

The cells were detached with trypsin/EDTA in a state where ASC became confluent on a 10 cm plate, and washed once with PBS(−). Since innumerable cell clusters were formed in some plates, they were determined to be differentiated cells. All the cells were suspended in PBS(−) at $1×10^6$/ml and cryopreserved at −20° C. The cell fluid was thawed in hot water at 38° C. or at room temperature and treated as follows.

(a) The cell fluid was used for co-culture as it was (disrupted ASC cell suspension).

(b) After centrifugation, the supernatant was collected (ASC centrifuged supernatant).

(c) The supernatant after centrifugation was filtered through a cellulose acetate membrane filter (pore size 0.2 μm) (ASC supernatant filtrate).

The ASC solutions of (a) to (c) were diluted with PBS so as to have various concentrations in terms of number of cells.

1-3. Co-Culture of ASC Solution and Bovine Frozen-Thawed Semen

100 μl of each ASC solution and 100 μl of thawed frozen semen (about $1×10^8$ cells/ml) were mixed and placed in a 24-well plate, and co-cultured in a $CO_2$ incubator (5% $CO_2$, 95% air, 39° C., saturated humidity). The culture time was set to 0 hours, 3 hours, 6 hours, 9 hours, 14 hours, 16 hours, and 18 hours, and ASC solutions with the following cell concentrations were used.

Disrupted ASC cell suspension: 1, 10, or $100×10^4$ cells/ml (first time); 10, 50, 75, or $100×10^4$ cells/ml (second time)

ASC centrifuged supernatant: 1 or $10×10^4$ cells/ml

ASC supernatant filtrate: 1, 10, or $100×10^4$ cells/ml 1-4. Evaluation of Sperm Motility After culture for a predetermined period of time, motile sperms were observed under a phase contrast microscope, and it was determined which of the following states most of the motile sperms was in.

+++: Active progressive motion (advancing a length equal to or longer than the major axis of the head with one reciprocation of the tail)

++: Motion in which the head rotates while progressiveness is weak

+: Weak motion with the head not rotating

−: No motile sperm is observed

2. Results

The results are shown below. An effect of increasing sperm motility is observed in the disrupted ASC cell suspension, ASC centrifuged supernatant, and ASC supernatant filtrate.

TABLE 2

| Treatment of cell fluid | Cell concentration (10,000 cells/ml) | 0 h | 3 h | 6 h | 9 h | 14 h | 16 h | 18 h |
|---|---|---|---|---|---|---|---|---|
| Control group (PBS) | 0 | +++ | ++ | + | − | | | |
| Disrupted cell suspension | 100 | +++ | +++ | +++ | +++ | | | |
| Disrupted cell suspension | 10 | +++ | +++ | ++ | ++ | | | |
| Disrupted cell suspension | 1 | +++ | ++ | + | − | | | |
| Centrifuged supernatant | 10 | +++ | +++ | ++ | ++ | | | |
| Centrifuged supernatant | 1 | +++ | ++ | + | − | | | |
| Supernatant filtrate | 100 | +++ | +++ | +++ | +++ | | | |
| Supernatant filtrate | 10 | +++ | +++ | ++ | ++ | | | |
| Supernatant filtrate | 1 | +++ | ++ | + | − | | | |
| Disrupted cell suspension | 100 | | | | | +++ | ++ | ++ |
| Disrupted cell suspension | 75 | | | | | ++ | ++ | + |
| Disrupted cell suspension | 50 | | | | | ++ | ++ | + |
| Disrupted cell suspension | 10 | | | | | + | − | − |

<Test 3> Effect of ASC Filtrate on Collection of Bovine Internally Embryos 1. Materials and Methods 1-1. Production of ASC Filtrate ASC cultured and proliferated under the above-described method and conditions was resuspended in PBS to $100 \times 10^4$ cells/ml and frozen at $-20°$ C. Thereafter, the frozen product was thawed at room temperature and filtered through a filtration sterilization filter of a cellulose acetate membrane with a pore size of 0.2 μm, and the filtrate was collected (called "ASC filtrate"). The ASC filtrate was filled and sealed in a 0.5 ml capacity straw for semen cryopreservation and cryopreserved at $-20°$ C.

1-2. Superovulation Treatment of Japanese Black Cattle

With the estrus induced day as day 0, an intravaginal indwelling progesterone preparation (CIDR) was inserted into the vagina of a cow 11 days before. Superovulation treatment was performed by tapered administration of anterior lobe follicle-stimulating hormone (FSH: Antrin, Kyoritsu Seiyaku Corporation). Specifically, administration was performed 2.5 ml of FSH (twice in the morning and afternoon) 4 days before estrus, 1.5 ml of FSH (twice in the morning and afternoon) 3 days before, and 1 ml of FSH and 2 ml of PG (twice in the morning and afternoon) 2 days before. Furthermore, the CIDR was removed in the morning two days before.

1-3. Artificial Insemination

Artificial insemination was performed once in the afternoon on the estrus day. The frozen semen was thawed with hot water at 38° C. and injected into a uterine body using an artificial inseminator. Subsequently, in the test group, the thawed ASC filtrate (0.5 ml) was injected into the uterine body using an artificial inseminator. In the control group, PBS (0.5 ml) was injected.

1-4. Collection of Embryos

Eight days after estrus, embryos were collected by refluxing the left and right uterine horns. A balloon catheter was inserted into the uterus and fixed to the base of the uterine horn, and 30 to 40 ml of a lactated Ringer's solution (Haruzen; Nippon Zenyaku Kogyo Co., Ltd.) supplemented with 0.5% fetal calf serum (FCS) and penicillin as well as streptomycin was injected into the uterine horn, and then the discharged liquid was collected in a light shielding bottle. By repeating this at the left and right uterine horns about 12 times, the uterine horn was refluxed. The reflux liquid was filtered with an Em-Con filter and concentrated, and a embryo was searched under a stereoscopic microscope.

1-5. Evaluation of Embryos

The developmental stage and quality as well as the number of the collected embryos were examined. The developmental stage was classified into expanded blastocyst (EXB), blastocyst (B), early blastocyst (EB), compacted morula (CM), degraded, and unfertilized. Among embryos that did not develop beyond compacted morula, those that stopped development due to normal division or abnormal division were regarded as degraded, and those that were not divided were regarded as unfertilized. The quality of embryos was determined according to the LETS manual. It was determined that those with no denatured portion was determined as Excellent, those with a denatured portion of equal to or less than 15% as Good, those with a denatured portion of equal to or less than 50% as Fair, and those with a denatured portion of equal to or less than 75% as Poor. Degraded and unfertilized were determined as Dead.

1-6. Number of Tests

Two cows were subjected to superovulation treatment in one test, and embryo collection was performed with one cow as a test group and the other one as a control group. After embryo collection, the same cows were subjected to superovulation treatment at intervals of about 1 month, and the test group and the control group were exchanged for embryo collection. This was done with 3 couples of 6 cows, and the results of embryo collection for 6 test groups and 6 control groups were tallied.

2. Results

The results are shown below (Tables 3 and 4). Compared with the control group, in the test group, the number of collected embryos was large, the developmental stage and quality were also high.

TABLE 3

|  | Test group | Control group |
| --- | --- | --- |
| Expanded blastocyst | 23 (36%) | 2 (6%) |
| Blastocyst | 16 (25%) | 4 (13%) |
| Early blastocyst | 7 (11%) | 5 (16%) |
| Compacted morula | 1 (2%) | 4 (13%) |
| Regression | 13 (20%) | 7 (21%) |
| Unfertilization | 4 (6%) | 10 (31%) |
| Total | 64 (100%) | 32 (100%) |

TABLE 4

|  | Test group | Control group |
| --- | --- | --- |
| Excellent | 28 (44%) | 2 (6%) |
| Good | 11 (17%) | 4 (13%) |
| Fair | 6 (9%) | 4 (13%) |
| Poor | 2 (3%) | 5 (16%) |
| Dead | 17 (27%) | 17 (53%) |
| Total | 64 (100%) | 32 (100%) |

B. Test in Holstein Dairy Cattle

<Test 1> Collection Results of In-Vivo Embryos Utilizing "Sex-Sorted Semen Supplemented with Adipose Stem Cell Fluid"

In artificial insemination when superovulation treatment was performed to produce in-vivo embryos, the results of in-vivo embryo collection were compared between the case where ASC was added to sex-sorted semen and the case where ASC was not added. A group to which ASC was added to sex-sorted semen was used as a test group, a group to which ASC was not added (group to which PBS was added) was used as a control group. Collection of in-vivo embryos was done twice, and in fertilization of the first embryo collection, semen was injected into deep parts of uterine horns using a right uterine horn as a test group and a left uterine horn as a control group. In the second embryo collection, using the right uterine horn as a control group and the left uterine horn as a test group, deep injection was performed on the left and right as in the first time.

1. Materials and Methods 1-1. Test Cattle

Name: Chelsea (individual identification number: 1338723678)

Birth date: Feb. 29, 2012

Final delivery: Mar. 26, 2014 (primiparity)

Past embryo collection results (postpartum): Sep. 1, 2014 (collected number:

5, number of normal embryos: 3 (Excellent and Good: 3)), Nov. 6, 2014 (collected number: 14, number of normal embryo s: 10 (Excellent and Good: 8, Fair: 2))

1-2. Superovulation Treatment Method

At any time of estrous cycle, intravaginal indwelling progesterone preparation (CIDR) was inserted into the vagina and 1 ml of estradiol benzoate (EB: Ovahormon) was injected intramuscularly. With this day as 0th day, the anterior lobe follicle-stimulating hormone (FSH: Antrin, Kyoritsu Seiyaku Corporation) was administered twice a day (9 o'clock in the morning and 5 o'clock in the evening) for 3 days from the 4th day to the 6th day by tapered administration (6 AU per dose on 4th day, 4 AU per dose on 5th day, and 3 AU per dose on 6th day). On the morning of the 7th day, FSH 2 AU and 3 ml of prostaglandin F2α (PG: Dalmazin, Kyoritsu Seiyaku Corporation) were administered, and in the evening on the same day, FSH 2 AU was administered and CIDR was removed. At 4 pm on the following day, 4 ml of gonadotropin-releasing hormone (GnRH; Spornen, Kyoritsu Seiyaku Corporation) (200 μg as fertirelin acetate) was administered. Artificial insemination was performed 24 hours after administration of GnRH, and embryo collection was performed one week later. Also, the interval between the first and second embryo collection was 87 days.

Figure 2:
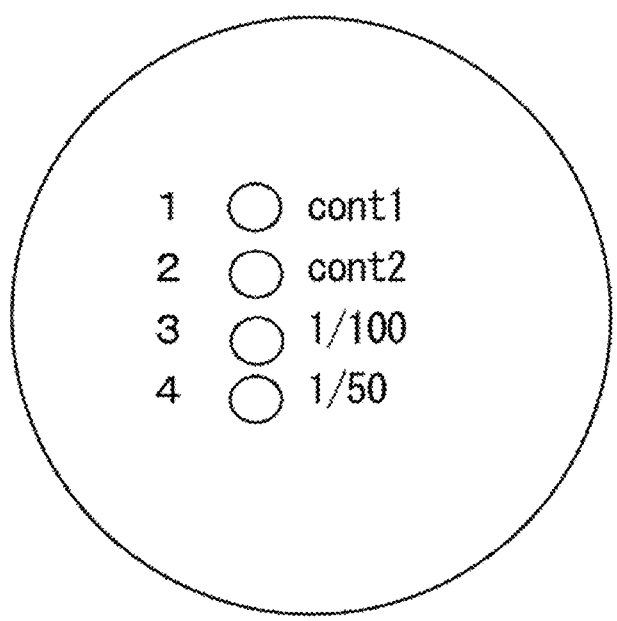
FIG. 2 A schematic diagram of a petri dish used for a culture test. cont 1: semen 20 µl+PBS 3 µl, cont 2: semen 20 µl+PBS 6 µl, 1/100: semen 20 µl+ASC filtrate 3 µl, 1/50: semen 20 µl+ASC filtrate 6 µl.

1-3. Preliminary Test for Determining Concentration when Adipose Stem Cell Fluid is Added to Sex-Sorted Semen In Test 2 "Effect of Japanese Black Cattle ASC Filtrate" in A. Test in Japanese Black Cattle, an effect of maintaining sperm motility was seen by adding ASC at a concentration equivalent to $1/100$ of the sperm count in the test with normal semen. In this experiment, in order to confirm the effect in sex-sorted semen, an effect of ASC filtrate at a concentration equivalent to $1/100$ and $1/50$ (the ASC filtrate prepared in Test 3 "Effect of ASC Filtrate on Collection of Bovine Internally Embryos" in A. Test in Japanese Black Cattle) on sex-sorted sperm motility was investigated. PBS was used as control (cont 1 and cont 2). As the sex-sorted semen (in the straw), "RCA athlete two six" (JP5H54411X) of Livestock Improvement Association of Japan, Inc on Nov. 12, 2012 (a two-layer straw containing frozen semen with 3 million sperms per straw and a diluent layer with an air layer in between) was used. After thawing in warm water at 37° C., only the liquid layer containing sperms (about 200 μl) was pushed out into a petri dish and tested. As shown in FIG. 2, a culture test was performed in the petri dish. After culture for various time periods, the ratio of sperms showing progression (sperm moving forward) and motion (sperm not progressing but moving) about sperm motility was classified into 4 levels (−, +, ++, +++). The ASC concentration in the ASC filtrate added was equivalent to 1 million/ml. The cell suspension was covered with mineral oil and cultured on a warm plate at 37° C. for up to 28 hours.

cont 1: semen 20 μl+PBS 3 μl
cont 2: semen 20 μl+PBS 6 μl
$1/100$: semen 20 μl+ASC filtrate 3 μl
$1/50$: semen 20 μl+ASC filtrate 6 μl Since 3 million sperms are contained in 200 μl of sex-sorted semen, 300,000 sperms are contained in 20 μl. Therefore, equivalent to $1/100$ of 300,000 sperms is 3 μl of ASC filtrate (1 million/ml) (equivalent to 1000 ASCs), equivalent to $1/50$ of the same is 6 μl of ASC filtrate.

1-4. Method of Treating Semen Used for Artificial Insemination

Four frozen semen straws of seed bull name "O-K Farm Heart Lancaster ET" (JP5H53562X) of Livestock Improvement Association of Japan, Inc on Apr. 7, 2014 (two-layer straws containing a frozen semen layer with 6 million sperms per straw and a diluent layer with an air layer in between, sold for embryo collection) were used. The amount of liquid containing sperms was about 200 μl/straw. Embryo collection was performed two times using two straws per embryo collection (4 in total) since one straw of semen was each injected into the left and right uterine horns (for the test group and for the control group).

Thawing of the frozen semen was treated with hot water of 37° C. for about 30 seconds. As semen treatment, after the thawing, only the semen layer was pushed out into a petri dish for both semen for the test group and semen for the control group, 60 μl of the ASC filtrate was added to the semen for the test group and mixed, and 60 μl of PBS was added to the semen for the control group and mixed. After mixing, another 0.5 ml capacity straw was refilled and subsequently filled with a small amount of air layer, then refilled with the diluent layer in the original straw, and it was kept warm at 37° C. to 38° C. until injected into the uterus.

1-5. Artificial Insemination

Using "mo-No. 5" (Misawa Medical Industry Co., Ltd.) as an injector, in the first embryo collection, the semen for the test group was injected into a deep part of a right uterine horn and the semen for the control group was injected into a deep part of a left uterine horn. Conversely, in the second embryo collection, the semen for the test group was injected into the deep part of the left uterine horn, and the semen for the control group was injected into the deep part of the right uterine horn (at the point where a tip of the injector was inserted from the uterine body to the uterine horn by about 5 cm, a tube was pushed into the deep part by about 20 cm, and the semen was injected).

1-6. Embryo Collection

The left and right uterine horns were separately perfused with lactated Ringer's supplemented with 0.5% calf serum (CS).

2. Results 2-1. Results of Preliminary Test

As shown in Table 5, progressing sperms were no longer observed after 9 hours after thawing in both control groups (cont 1, cont 2), but progressing sperms were observed until 12 hours in both test groups ($1/100$, $1/50$). Since the results were about the same for $1/100$ and $1/50$, it was decided to perform the subsequent experiment at $1/100$.

TABLE 5

| Group | 0 h | | 3 h | | 6 h | | 9 h | | 12 h | | 24 h | | 28 h | |
|---|---|---|---|---|---|---|---|---|---|---|---|---|---|---|
| | Progression | Motion | Progression | Motion | Progression | Motion | Progression | Motion | Progression | Motion | Progression | Motion | Progression | Motion |
| cont 1 | +++ | +++ | +++ | +++ | +++ | +++ | − | +++ | − | ++ | − | − | − | − |
| cont 2 | +++ | +++ | +++ | +++ | +++ | +++ | − | +++ | − | ++ | − | − | − | − |
| $1/100$ | +++ | +++ | +++ | +++ | +++ | +++ | +++ | +++ | ++ | +++ | − | + | − | − |
| $1/50$ | +++ | +++ | +++ | +++ | +++ | +++ | +++ | +++ | ++ | +++ | − | + | − | − |

2-2. Results of Embryo Collection

Figure 3:
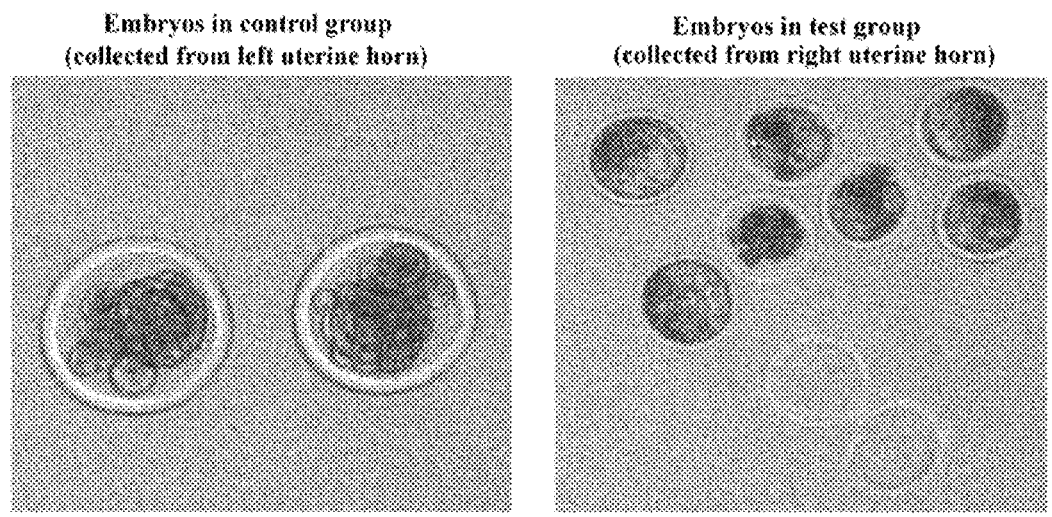
FIG. 3 Results of first embryo collection. Left: embryos in control group (collected from left uterine horn), right: embryos in test group (collected from right uterine horn).
Figure 4:
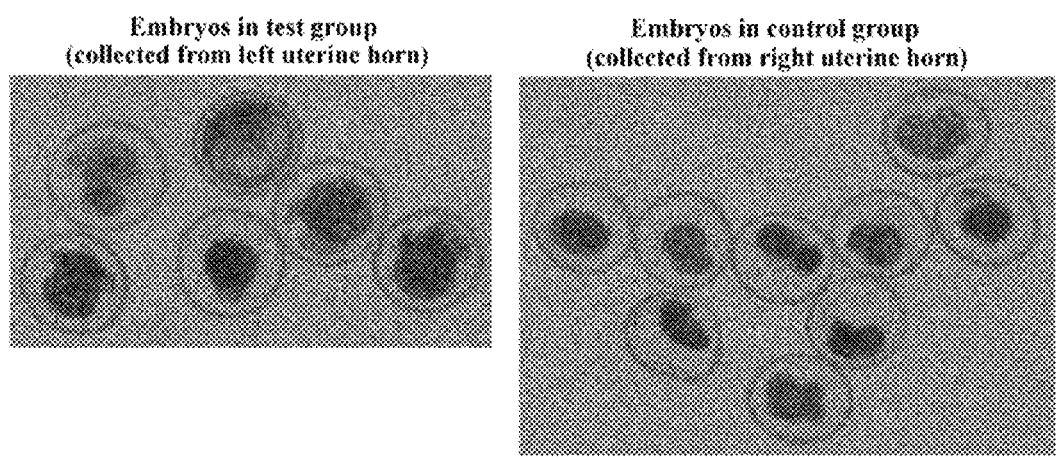
FIG. 4 Results of second embryo collection. Left: embryos in test group (collected from left uterine horn), right: embryos in control group (collected from right uterine horn).

The developmental stage was classified into expanded blastocyst (EXB), blastocyst (B), early blastocyst (EB), compacted morula (CM), degraded, and unfertilized. In addition, as to quality, Excellent and Good were indicated by A, Fair was indicated by B, and Poor was indicated by C. Degraded and unfertilized were determined as Dead. As shown in Tables 6 and 7, and FIGS. 3 and 4, the number of collected embryos was almost the same as 11 in the control group and 13 in the test group, but the number of normal embryos was 2 in the control group and 11 in the test group, which was large in the test group. It seems that, by adding the ASC filtrate to sex-sorted semen which is said to be small in the number of sperms per straw compared with general semen and have problems with vitality, the fertilization rate improved, the number of normal embryos and the normal embryo rate improved.

Test group 2 (transferred on Jun. 26, 2015): An apparently normal child was born on Mar. 29, 2016.

Test group 3 (transferred on Aug. 19, 2015): An apparently normal child was born in May, 2016.

C. Sperm Activation by Suspensions of Various Disrupted Stem Cells

Whether or not the same effect as the sperm activating effect observed in the disrupted suspension of adipose tissue-derived stem cells (ASC) was observed in other mesenchymal stem cells was examined.

1. Materials and Methods 1-1. Preparation of Filtrates of Various Mesenchymal Stem Cells Human adipose tissue-derived stem cells (H-ASC), human dental pulp-derived stem cells (H-DPSC), human bone marrow-derived stem cells (H-BM-MSC), and human

TABLE 6

Stage of collected embryo

| | Stage | EXB | B | EB | CM | Denaturation | Total | Number of normal embryos | Normal embryos rate | |
|---|---|---|---|---|---|---|---|---|---|---|
| Control group | First control group (left uterine born) | 0 | 0 | 0 | 2 | 0 | 2 | 2 | 100.0% | (2/2) |
| | Second control group (right uterine born) | 0 | 0 | 0 | 0 | 9 | 9 | 0 | 0.0% | (0/9) |
| | Total | 0 | 0 | 0 | 2 | 9 | 11 | 2 | 18.2% | (2/11) |
| | Percentage in normal embryos | 0.0% | 0.0% | 0.0% | 100.0% | | | | | |
| Test group | First test group (left uterine born) | 0 | 2 | 2 | 1 | 0 | 7 | 7 | 100.0% | (7/7) |
| | Second test group (right uterine born) | 0 | 4 | 0 | 3 | 2 | 6 | 4 | 66.7% | (4/6) |
| | Total | 0 | 6 | 2 | 4 | 2 | 13 | 11 | 84.0% | (11/13) |
| | Percentage in normal embryos | 0.0% | 45.5% | 18.2% | 36.4% | | | | | |

TABLE 7

Quality of collected embryo

| | Rank | A | B | C | Denaturation | Total | Number of normal embryos |
|---|---|---|---|---|---|---|---|
| Control group | First control group (left uterine born) | 0 | 0 | 0 | 0 | 2 | 2 |
| | Second control group (right uterine born) | 0 | 0 | 0 | 9 | 9 | 0 |
| | Total | 0 | 0 | 0 | 9 | 11 | 2 |
| | Percentage in normal embryos | 0.0% | 100.0% | 0.0% | | | |
| Test group | First test group (left uterine born) | 7 | 0 | 0 | 0 | 7 | 7 |
| | Second test group (right uterine born) | 1 | 8 | 0 | 2 | 6 | 4 |
| | Total | 8 | 8 | 0 | 2 | 13 | 11 |
| | Percentage in normal embryos | 72.7% | 27.3% | 0.0% | | | |

Transfer results of the collected embryos were as follows.

Embryos in the control group: 1 out of 2 normal embryos was transferred and conceived. Conception rate 100% (1/1).

Embryos in the test group: 6 out of 11 normal embryos were transferred, and 3 were conceived. Conception rate 50% (3/6).

On the other hand, the results of childbirth (parturition) were as follows.

Control group (transferred on Feb. 16, 2015): An apparently normal child was born on Nov. 16, 2015.

Test group 1 (transferred on Jun. 26, 2015): An apparently normal child was born on Mar. 27, 2016.

umbilical cord blood-derived stem cells (H-CB-MSC) that had been prepared by a conventional method and cryopreserved were thawed and then centrifuged (1500 rpm, 5 minutes). The supernatant was filtered through a cellulose acetate membrane filter (pore size 0.2 μm) to obtain filtrates of each stem cell (filtrate of the human adipose tissue-derived stem cells: H-ASC-f2, filtrate of the human dental pulp-derived stem cells: H-DPSC-f2, filtrate of the human bone marrow-derived stem cells: H-BM-MSC-f2, filtrate of the human umbilical cord blood-derived stem cells: H-CB-MSC-f2). A part of each filtrate was cryopreserved at −80° C., thawed and then used for experiments (H-DPSC-f1, H-DPSC-f1, H-BM-MSC-f1, H-CB-MSC-f1). For a positive control (PC), filtrate of bovine adipose tissue-derived stem cells (B-ASC-f1) obtained by the same treatment (centrifugation after freezing and thawing, filter filtration, then cryopreservation, and thawing again) was used.

particular, the human DPSC filtrate was observed to have almost the same effect as the bovine ASC filtrate. Incidentally, the presence or absence of refreezing after filter filtration had no significant effect on the sperm activating effect.

TABLE 8

| | Added solution | Addition amount μl | Elapsed time (h) | | | | | | | | |
|---|---|---|---|---|---|---|---|---|---|---|---|
| | | | 0 | 1.5 | 3 | 4.5 | 6 | 7.5 | 9 | 10.5 | 12 |
| NC | PBS(−) | 100 | +++ | +++ | +++ | ++ | ++ | + | ± | − | − |
| PC | B-ASC-f1 | | | +++ | +++ | +++ | +++ | +++ | ++ | ++ | ++ |
| Adipose | H-ASC-f1 | | | +++ | +++ | +++ | +++ | ++ | ++ | ++ | + |
| | H-ASC-f2 | | | +++ | +++ | +++ | +++ | ++ | ++ | ++ | + |
| Dental pulp | H-DPSC-f1 | | | +++ | +++ | +++ | +++ | +++ | ++ | ++ | ++ |
| | H-DPSC-f2 | | | +++ | +++ | +++ | +++ | +++ | ++ | ++ | ++ |
| Bone | H-BM-MSC-f1 | | | +++ | +++ | +++ | +++ | ++ | ++ | ++ | + |
| marrow | H-BM-MSC-f2 | | | +++ | +++ | +++ | +++ | ++ | ++ | ++ | + |
| Umbilical | H-CB-MSC-f1 | | | +++ | +++ | +++ | +++ | ++ | ++ | ++ | + |
| cord blood | H-CB-MSC-f2 | | | +++ | +++ | +++ | +++ | ++ | ++ | ++ | + |
| NC | PBS(−) | 50 | +++ | +++ | +++ | ++ | + | ± | − | − | − |
| PC | B-ASC-f1 | | | +++ | +++ | +++ | +++ | ++ | + | + | ± |
| Adipose | H-ASC-f1 | | | +++ | +++ | +++ | ++ | ++ | + | + | ± |
| | H-ASC-f2 | | | +++ | +++ | +++ | ++ | ++ | ± | ± | − |
| Dental pulp | H-DPSC-f1 | | | +++ | +++ | +++ | ++ | ++ | + | + | + |
| | H-DPSC-f2 | | | +++ | +++ | +++ | ++ | ++ | + | + | ± |
| Bone | H-BM-MSC-f1 | | | +++ | +++ | +++ | ++ | ++ | + | ± | − |
| marrow | H-BM-MSC-f2 | | | +++ | +++ | +++ | ++ | ++ | + | ± | − |
| Umbilical | H-CB-MSC-f1 | | | +++ | +++ | +++ | ++ | ++ | + | ± | − |
| cord blood | H-CB-MSC-f2 | | | +++ | +++ | +++ | ++ | ++ | + | ± | − |

1-2. Co-culture of Stem Cell Filtrate and Bovine Frozen-Thawed Semen

Each stem cell filtrate (100 μl or 50 μl) was added to wells of a 24-well plate. Meanwhile, bovine frozen semen (6 same lots) was thawed in a conventional manner (38° C., 45 sec) and mixed in a tube (total 3 ml), then was dispensed to each well by a specified amount. The 24-well plate was transferred to a $CO_2$ incubator (5% $CO_2$, 95% air, 38° C., saturated humidity) and co-cultured.

1-3. Evaluation of Sperm Motility (Visual Evaluation)

After culture for predetermined times (after 0 hours, 1.5 hours, 3 hours, 4.5 hours, 6 hours, 7.5 hours, 9 hours, 10.5 hours, and 12 hours), motile sperms were observed under a phase contrast microscope, and which of the following state most of the motile sperms was in was determined.

+++: Active progressive motion (advancing a length equal to or longer than the major axis of the head with one reciprocation of the tail)

++: Motion in which the head rotates while progressiveness is weak

+: Weak motion with the head not rotating

±: Almost immobile, but with a few mobile sperm

−: No motile sperm is observed 1-4. Evaluation of Sperm Motility (Analysis of Travel Distance)

At the time of visual observation (after 1.5 hours, 3 hours, 4.5 hours, 6 hours, 7.5 hours, 9 hours), a moving image of 30 seconds was taken with a camera attached to the microscope. Moving image data was converted and processed, imported into ImageJ software, and the travel distance of sperm was analyzed.

2. Results

Figure 5:
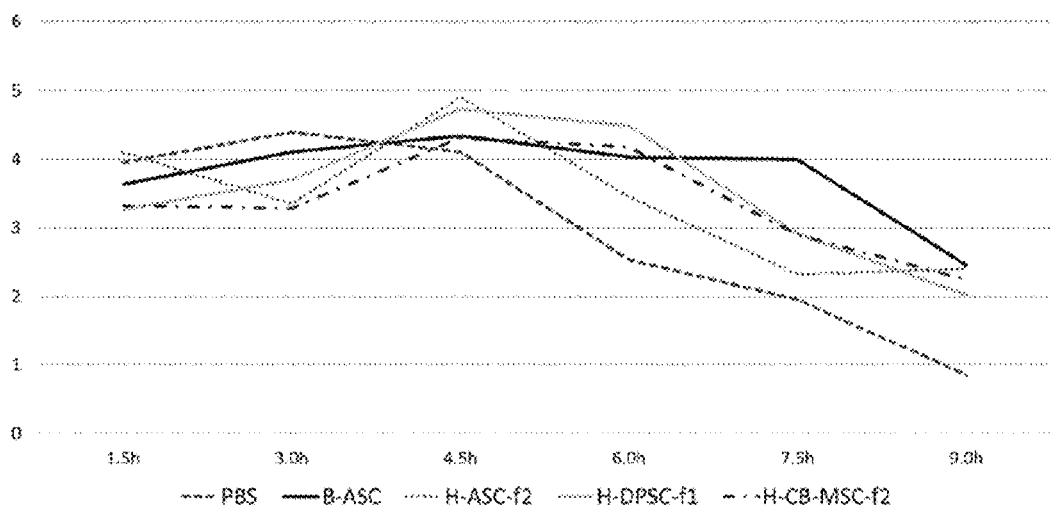
FIG. 5 A sperm activating effect of filtrate of various mesenchymal stem cells. The average travel distances per frame were compared. PBS: addition of PBS(−) (negative control), B-ASC: addition of bovine adipose tissue-derived stem cell filtrate (positive control), H-ASC-f2: addition of human adipose tissue-derived stem cell filtrate, H-DPSC-f1: addition of freeze-thawed human dental pulp-derived stem cell filtrate, H-CB-MSC-f2: addition of human umbilical cord blood-derived stem cell filtrate.

The results of visual observation are shown below. While the bovine ASC filtrate (B-ASC) showed the strongest bovine sperm activating effect, other mesenchymal stem cell filtrates also showed bovine sperm activating effect. In The analysis results of the travel distances of sperms (comparison of average travel distance per frame) are shown in FIG. 5. As with visual observation results, all mesenchymal stem cell filtrates also increased bovine sperm motility.

D. Analysis of Sperm Activating Component

Based on the results of the above experiments, it was hypothesized that proteinaceous factors are involved in sperm activation of disrupted ASC cell suspension, and attempted to verify it. First, a disrupted ASC cell suspension filtered with a protein adsorption filter did not enhance sperm motility. In contrast, in the case of a disrupted ASC cell suspension filtered with a protein non-adsorption filter, sperm motility was enhanced. Based on this result, protein components in the disrupted ASC cell suspension were analyzed by LCMS. As a result of the analysis, heat shock protein 90α (HSP90α) was identified as a component with a high content. Therefore, the HSP90α solution (dissolved in PBS at a concentration of 2 μg/ml, 10 μg/ml, or 50 μg/ml) was added to 50 μl of bovine semen at one time (addition of 50 μl at one time) or dividedly (addition of 10 μl after 0 hours, 2 hours, 4 hours, and 6 hours), and the mixture was cultured. After culture for predetermined times (after 0 hours, 2 hours, 4 hours, 6 hours, 7 hours, and 8 hours), motile sperms were observed under a phase contrast microscope, and which of the following state most of the motile sperm was in was determined.

⊚: Progressive motion with head rotating

○: Weak motion with head not rotating

Δ: Almost immobile, but with a few mobile sperms x: No motile sperm is observed

In addition, in a case where a slight difference in motility was observed in visual observation while the same determination was made according to the above criteria, the magnitude of relative motility was expressed by the number of plus (none, +, ++, +++).

The test results are shown below. HSP90α did not prolong survival time, but increased vitality of sperm in a concentration-dependent manner. According to this result, it can be said that a sperm activator can be constituted using HSP90α as an active ingredient.

TABLE 9

| Concentration of HSP90α solution (In PBS) | Addition protocol | 0 h | 2 h | 4 h | 6 h | 7 h | 8 h |
|---|---|---|---|---|---|---|---|
| Control 1 | Add 50 μl of PBS at start of culture | ◎ | ◎ | ○ | △ | △ | x |
| 2 μg/ml | Add 50 μl of HSP90α solution at start of culture | ◎ | ◎ | ○ (+) | △ (+) | △ (+) | x |
| 10 μg/ml | Add 50 μl of HSP90α solution at start of culture | ◎ | ◎ | ○ (++) | △ (++) | △ (++) | x |
| 50 μg/ml | Add 50 μl of HSP90α solution at start of culture | ◎ | ◎ | ○ (+++) | △ (+++) | △ (+++) | x |
| Control 2 | Add 10 μl of PBS every 2 hours | ◎ | ◎ | ○ | △ | x | x |
| 2 μg/ml | Add 10 μl of HSP90α solution every 2 hours | ◎ | ◎ | ○ (+) | △ (+) | x | x |
| 10 μg/ml | Add 10 μl of HSP90α solution every 2 hours | ◎ | ◎ | ○ (++) | △ (++) | x | x |

E. Test in Pigs
<Test 1>
1. Method
1-1. Sperm

Sperm-rich fraction of semen collected from Duroc boar (1 pig; individual number D2003) was diluted with diluent (GP Long, Global Pig Farms, Inc.) and stored at 17° C. After storing the semen for 5 days, it was diluted with GP long so that the sperm concentration became $3 \times 10^7$/ml.

1-2. Filtrate

Porcine adipose stem cells (pASC) which became confluent by culturing in a flask were detached, centrifuged once with DPBS(−) at room temperature, then resuspended in DPBS(−), and cryopreserved at −30° C. The cells were disrupted by thawing at room temperature and centrifuged at room temperature at 200 G for 5 minutes. The supernatant was taken and caused to pass through a filtration sterilization filter with a pore size of 0.2 μm to obtain a pASC filtrate.

1-3. Culture and Evaluation of Motility and Agglutination of Sperm

The sperms and the pASC filtrate were mixed in a round bottom microtube (the same amount of DPBS(−) was added in the control without addition of the pASC filtrate), so that the final sperm concentration was $3 \times 10^7$/ml and the added cell concentration was 1/1,000 ($3 \times 10^4$/ml) or 1/100 ($3 \times 10^5$/ml), and cultured in a water bath at 38.5° C. for 0.25, 1, 10, 15 and 17.5 hours. After culture, some sperms were taken (3 μl) and placed in a counting chamber for sperm motility measurement (Leja, depth 20 μm) and heated to 38.5° C. The sperms were observed under a phase contrast microscope, and motility and agglutination were determined for the following items.

(1) Motility Rate (%)

The percentage of all motile sperms in total sperms was subjectively determined and defined as the motility rate.

(2) Rate of Progressive Motion (%)

The percentage of sperms moving at extremely fast speed while making head bright or sperms which move slowly but progressively occupied in total motile sperms was subjectively determined and defined as the rate of progressive motion.

(3) Activity of Motion

Activity of sperm motility was classified into 5 levels as follows.

0=Not moving at all (in this case, the motility rate is 0%)

1=A case where all or most sperms are in motion but do not move the position, and show extremely slow motion on the spot 2=A case where sperms make progressive or non-progressive motion (including circular motion) but the tail vibration is slow 3=A case where sperms make progressive or non-progressive motion (including circular motion) but the tail motion is relatively fast (the contour of the vibrating tail is seen)

4=A case where sperms make progressive or non-progressive motion (including circular motion) but the tail motion is extremely fast (the contour of the vibrating tail is too fast to be seen)

(4) Agglutination

The degree to which multiple sperms were connected at the head was determined in 5 levels as follows.

0=No agglutination is observed at all, or only slightly observed

1=A case where 25% or less of the sperms agglutinate

2=A case where 25 to 50% of the sperms agglutinate

3=A case where 50 to 75% of the sperms agglutinate

4=A case where 75% or more of the sperms agglutinate (5) Determination of Survival Rate According to the method of previous report (Harrison, R A, Vickers S E. Use of fluorescent probes to assessment membrane integrity in mammalian spermatozoa. J. Reprod. Fertil. 88 (1): 343-352 (1990).), the cultured sperms were subjected to propidium iodide staining. Two hundred sperms were observed under a fluorescence phase contrast microscope, and the survival rate (%) was calculated using a sperm in which the head was not colored red as a surviving sperm.

2. Results

As shown in Table 10 below, without addition of pASC filtrate, the motility rate increased at 1 to 10 hours of culture as compared to at 0.25 hours, and decreased after 10 hours. The rate of progressive motion increased at 1 to 15 hours of culture as compared to at 0.25 hours of culture and then decreased at 17.5 hours. On the other hand, in the addition of pASC filtrate, the motility rate and the rate of progressive motion increased at 10 and 15 hours of culture as compared to without addition. At 17.5 hours of culture, there was no difference in the motility rate and the rate of progressive motion between them. However, in motility at 17.5 hours of culture, progressively moving sperms without addition of pASC filtrate stopped progressive motion during observation, but progressively moving sperms with addition of filtrate progressively moved a longer distance. As to the activity and agglutination, no difference was observed regardless of the presence or absence of addition of pASC filtrate and the culture time.

TABLE 10

| Culture time (Time) | Addition concentration of pADSC filtrate* | Motility rate (%) | Rate of progressive motion (%) | Activity (0-4) | Agglutination (0-4) |
|---|---|---|---|---|---|
| 0.25 | 0 | 50 | 30 | 2 | 0 |
|  | $3 \times 10^4$/ml | 50 | 30 | 2 | 0 |
|  | $3 \times 10^5$/ml | 50 | 50 | 2 | 0 |
| 1 | 0 | 60 | 50 | 2 | 0 |
|  | $3 \times 10^4$/ml | 60 | 50 | 2 | 0 |
|  | $3 \times 10^5$/ml | 60 | 50 | 2 | 0 |
| 10 | 0 | 60 | 50 | 2 | 0 |
|  | $3 \times 10^4$/ml | 65 | 75 | 2 | 0 |
|  | $3 \times 10^5$/ml | 65 | 70 | 2 | 0 |
| 15 | 0 | 50 | 60 | 2 | 0 |
|  | $3 \times 10^4$/ml | 55 | 75 | 2 | 0 |
|  | $3 \times 10^5$/ml | 65 | 90 | 2 | 0 |
| 17.5 | 0 | 50 | 50$^a$ | 2 | 0 |
|  | $3 \times 10^4$/ml | 50 | 50$^b$ | 2 | 0 |
|  | $3 \times 10^5$/ml | 50 | 50 | 2 | 0 |

Influence of the addition of pASC filtrate (concentration of 1/100 and 1/1000 of sperm concentration) on the properties of Duroc boar sperm. *: The final sperm concentration is $3 \times 10^7$/ml. a: The progressively moving spermatozoa stop movement while observed. b: The progressively moving spermatozoa swam a longer distance than spermatozoa of 'a'.

<Test 2>
1. Method
1-1. Sperm

Sperm-rich fraction of semen collected from Duroc boar (1 pig; individual number D7302) was diluted with diluent (GP Long, Global Pig Farms, Inc.) and stored at 17° C. The semen stored for 5 days was diluted with GP long so that the sperm concentration became $2 \times 10^7$/ml.

1-2. Filtrate

The pASCs which became confluent by culturing in a flask were detached and centrifugally washed once with DPBS(−) at room temperature, and then resuspended in DPBS(−) to a concentration of $1.75 \times 10^6$/ml. The cells were disrupted by freezing at −30° C. and then thawing at room temperature and centrifuged at room temperature at 200 G for 5 minutes. The supernatant was taken and caused to pass through a filtration sterilization filter with a pore size of 0.2 µm to obtain a pASC filtrate. A stock solution ($1.75 \times 10^6$/ml) of pASC filtrate, a pASC filtrate obtained by diluting the stock solution with DPBS(−) equivalent to $2 \times 10^4$/ml, and a pASC filtrate obtained by diluting the same equivalent to $2 \times 10^5$/ml were used.

1-3. Culture and Evaluation of Motility and Agglutination of Sperm

Sperms ($2 \times 10^7$/ml) that had been resuspended in GP long dilution and DPBS(−) or a predetermined concentration of pASC filtrate (equivalent to $2 \times 10^4$/ml, $2 \times 10^5$/ml and $17.5 \times 10^5$/ml) were mixed at 1:1, so that the final sperm concentration was equivalent to $1 \times 10^7$/ml, and the final pASC addition concentration was equivalent to $0.1 \times 10^4$/ml (1/1,000 of the final sperm concentration), $1 \times 10^5$/ml (1/100 of the final sperm concentration), or $9 \times 10^5$/ml (1/11 of the final sperm concentration). The boar sperm mixed with the pASC filtrate were cultured in a water bath at 38.5° C. for 0.25, 1, and 7 hours. After culture, 10 µl of the sperms was taken, placed on a pre-warmed glass slide, and covered with a pre-warmed 18 mm×18 mm coverslip. The sperms were immediately observed under a phase contrast microscope of 200× magnification and 400× magnification, and motility and agglutination were determined as in Test 1.

2. Results

As shown in Table 11, without addition of pASC filtrate, the motility rate increased at 1 hour of culture as compared to at 0.25 hours, and decreased at 7 hours. The rate of progressive motion was 0% in any culture time. On the other hand, with the addition of pASC filtrate, the motility rate and the rate of progressive motion slightly increased in the pASC filtrate equivalent to $1 \times 10^4$/ml (50% vs 55% and 0 vs 0.5) as compared to the control at 1 hour of culture. In addition, while the motility rate at 7 hours of culture was 30% without addition of pASC filtrate, it increased with the addition equivalent to $1 \times 10^4$/ml and the addition equivalent to $9 \times 10^5$/ml of the filtrate (50% and 40%, respectively). As to the activity and agglutination, no difference was observed regardless of the presence or absence of addition of pASC filtrate and the culture time.

TABLE 11

| Culture time (Time) | Addition concentration of pADSC filtrate* | Motility rate (%) | Rate of progressive motion (%) | Activity (0-4) | Agglutination (0-4) |
|---|---|---|---|---|---|
| 0.25 | 0 | 40 | 0 | 1 | 0 |
|  | $1 \times 10^4$/ml | 40 | 0 | 1 | 0 |
|  | $1 \times 10^5$/ml | 40 | 0 | 1 | 0 |
|  | $9 \times 10^5$/ml | 40 | 0 | 1 | 0 |
| 1 | 0 | 50 | 0 | 1 | 0 |
|  | $1 \times 10^4$/ml | 55 | 0.5 | 1 | 0 |
|  | $1 \times 10^5$/ml | 50 | 0 | 1 | 0 |
|  | $9 \times 10^5$/ml | 50 | 0 | 1 | 0 |
| 7 | 0 | 30 | 0 | 1 | 0 |
|  | $1 \times 10^4$/ml | 50 | 0 | 1 | 0 |
|  | $1 \times 10^5$/ml | 30 | 0 | 1 | 0 |
|  | $9 \times 10^5$/ml | 40 | 0 | 1 | 0 |

Influence of the addition of pASC filtrate (concentration of 1/11, 1/100 and 1/1000 of sperm concentration) on the properties of Duroc boar sperm. *: The final sperm concentration is $1 \times 10^7$/ml.

<Discussion>

The action of pASC filtrate in the state that fresh semen to be used when porcine sperms were actually artificially inseminated was diluted with diluent was confirmed. In Test 1, increase in the motility rate and the rate of progressive motion by addition of pASC filtrate was confirmed at 10 and 15 hours of culture. Also, at 17.5 hours of culture, a sharp decline in motility was observed immediately after the start of observation, but progressively moving sperms without addition of filtrate stopped progressive motion during observation, whereas progressively moving sperms with addition of filtrate progressively moved a longer distance. This result shows that the pASC filtrate has sperm motility improving effect. In Test 2, while an effect of maintaining the motility rate and a slight increase in the rate of progressive motion by the pASC filtrate were observed, the difference was not dramatic. The reason for this is probably that since the rate of progressive motion at 0 hours of culture was 0%, recovery by pASC filtrate may be difficult in such samples. This is in contrast to the fact that, in Test 1, the rate of progressive motion, which was 30% at 0 hours of culture, increased after culture with addition of pASC filtrate rather than without addition.

INDUSTRIAL APPLICABILITY

The present invention is expected to make a great contribution in the livestock field and the reproductive medical care. For example, when the present invention is applied to transfer of embryo of beef cattle, normal embryos can be collected at a high rate, and more calves can be obtained. When the present invention is applied to artificial insemination of dairy cattle, the conception rate of sex-sorted semen can be improved. On the other hand, the present invention can also be used in treatment and improvement of male infertility, breeding and maintenance of species (for example, maintenance of endangered species, maintenance or crossing of pet lines), and the like, and the utility value is high.

The present invention is not limited to the description of the embodiments and examples of the invention. Various modified embodiments are also included in the present invention as long as they are easily conceivable by those skilled in the art without departing from the scope of claims. The contents of the articles, unexamined patent publications, patent applications, and the like specified herein are hereby incorporated herein by reference.

The invention claimed is:

1. A preparation for artificial insemination, comprising a sperm activator and semen, wherein the sperm activator's active ingredient is a filtrate obtained by filtering a disrupted product of one or more cells selected from the group consisting of adipose tissue-derived stem cells, dental pulp-derived stem cells, bone marrow-derived stem cells, and umbilical cord blood-derived stem cells.

2. An artificial insemination method, comprising injecting the preparation for artificial insemination according to claim 1 into a uterus of a non-human mammal.

3. The artificial insemination method according to claim 2, wherein the semen is sex-sorted semen.

4. A method for producing a fertilized egg by the artificial insemination method according to claim 2.

5. An in-vitro fertilization method, comprising adding the preparation for artificial insemination according to claim 1 to an ovum in vitro.

6. A sperm activation method, comprising the following step (1):
   (1) culturing semen in the presence of the sperm activator, the semen in the presence of the sperm activator forming the preparation for artificial insemination according to claim 1.

7. The sperm activation method according to claim 6, further comprising the following step (2):
   (2) recovering cultured semen.

8. A preparation for artificial insemination, comprising a mixture of a sperm activator and semen filled in a container, wherein the sperm activator's active ingredient is a filtrate obtained by filtering a disrupted product of one or more cells selected from the group consisting of adipose tissue-derived stem cells, dental pulp-derived stem cells, bone marrow-derived stem cells, and umbilical cord blood-derived stem cells.

* * * * *